US012594128B2

(12) United States Patent
Gustafson et al.

(10) Patent No.: US 12,594,128 B2
(45) Date of Patent: Apr. 7, 2026

(54) LOCKING AND DRIVE MECHANISMS FOR POSITIONING AND STABILIZATION OF CATHETERS AND ENDOSCOPIC TOOLS

(71) Applicant: Covidien LP, Mansfield, MA (US)

(72) Inventors: Evan M. Gustafson, Minneapolis, MN (US); Nathan J. Knutson, Long Lake, MN (US); Franklin J. Burquest, Crystal, MN (US)

(73) Assignee: Covidien LP, Mansfield, MA (US)

( * ) Notice: Subject to any disclaimer, the term of this patent is extended or adjusted under 35 U.S.C. 154(b) by 926 days.

(21) Appl. No.: 17/742,242

(22) Filed: May 11, 2022

(65) Prior Publication Data

US 2022/0378513 A1     Dec. 1, 2022

Related U.S. Application Data

(60) Provisional application No. 63/194,116, filed on May 27, 2021.

(51) Int. Cl.
| | |
|---|---|
| *A61B 34/20* | (2016.01) |
| *A61B 5/06* | (2006.01) |
| *A61B 10/04* | (2006.01) |
| *A61B 34/10* | (2016.01) |
| *A61M 25/01* | (2006.01) |

(52) U.S. Cl.
CPC .............. *A61B 34/20* (2016.02); *A61B 5/062* (2013.01); *A61B 10/04* (2013.01); *A61M 25/0113* (2013.01); *A61M 25/0147* (2013.01); *A61B 2034/105* (2016.02); *A61B 2034/2051* (2016.02)

(58) Field of Classification Search
CPC ......... A61B 34/20; A61B 5/062; A61B 10/04; A61B 2034/105; A61B 2034/2051; A61M 25/0113; A61M 25/0147
See application file for complete search history.

(56) References Cited

U.S. PATENT DOCUMENTS

| | | | |
|---|---|---|---|
| 5,069,206 A | 12/1991 | Crosbie | |
| 5,797,835 A | 8/1998 | Green | |
| 5,957,941 A | 9/1999 | Ream | |
| 6,533,761 B2 | 3/2003 | Bertoch et al. | |
| 6,755,191 B2 | 6/2004 | Bertoch et al. | |
| 6,974,465 B2 | 12/2005 | Belef et al. | |
| 7,637,863 B2 | 12/2009 | Deal et al. | |
| 7,891,621 B1 * | 2/2011 | Secora ................. | F16M 11/046 |
| | | | 248/292.12 |
| 7,927,271 B2 | 4/2011 | Dimitriou et al. | |
| 8,317,744 B2 | 11/2012 | Kirschenman | |
| 9,095,681 B2 | 8/2015 | Wenderow et al. | |
| 9,107,674 B2 | 8/2015 | Gaiser et al. | |
| 9,205,229 B2 | 12/2015 | Khalaj | |
| 9,259,305 B2 | 2/2016 | Fung et al. | |
| 9,289,266 B2 | 3/2016 | Weitzner et al. | |
| 9,302,090 B2 | 4/2016 | Williams et al. | |
| 9,445,714 B2 | 9/2016 | Vazales et al. | |
| 9,474,874 B2 | 10/2016 | Stephenson et al. | |

(Continued)

*Primary Examiner* — Sean A Frith

(74) *Attorney, Agent, or Firm* — Weber Rosselli & Cannon LLP

(57) ABSTRACT

A cannister system for containing a catheter, the cannister including a drive mechanism for driving the catheter from the cannister and into a luminal network of a patient, the cannister including an entrance point for insertion of a tool into the catheter.

20 Claims, 4 Drawing Sheets

(56)           References Cited

U.S. PATENT DOCUMENTS

| | | | |
|---|---|---|---|
| 9,668,639 B2 | 6/2017 | Meloul | |
| 9,731,096 B2 | 8/2017 | Bian et al. | |
| 9,855,101 B2 | 1/2018 | Wenderow et al. | |
| 10,046,130 B2 | 8/2018 | Molden et al. | |
| 10,201,264 B2 | 2/2019 | Golden et al. | |
| 10,238,845 B2 | 3/2019 | Ha et al. | |
| 10,357,634 B2 | 7/2019 | Simmons et al. | |
| 10,383,509 B2 | 8/2019 | Greenburg et al. | |
| 10,456,025 B2 | 10/2019 | Hung et al. | |
| 10,500,361 B2 | 12/2019 | Phillips et al. | |
| 10,588,495 B2 | 3/2020 | Simmons et al. | |
| 10,667,673 B2 | 6/2020 | Su et al. | |
| 2007/0083184 A1* | 4/2007 | Simpson | A61M 25/0113 |
| | | | 604/500 |
| 2013/0096497 A1* | 4/2013 | Duindam | A61M 25/0133 |
| | | | 604/95.01 |
| 2014/0039465 A1* | 2/2014 | Schulz | A61M 60/414 |
| | | | 604/528 |
| 2014/0262882 A1* | 9/2014 | Barnell | B29C 49/00 |
| | | | 264/534 |
| 2014/0276948 A1* | 9/2014 | Zirps | A61M 25/09041 |
| | | | 606/130 |
| 2019/0000568 A1* | 1/2019 | Connolly | A61B 1/2676 |
| 2019/0111236 A1* | 4/2019 | Oliverius | A61M 25/0136 |
| 2020/0046433 A1* | 2/2020 | Krimsky | A61B 34/20 |

\* cited by examiner

LOCKING AND DRIVE MECHANISMS FOR POSITIONING AND STABILIZATION OF CATHETERS AND ENDOSCOPIC TOOLS

CROSS-REFERENCE TO RELATED APPLICATION

The present application claims the benefit of and priority to U.S. Provisional Patent Application Ser. No. 63/194,116, filed on May 27, 2021, the entire content of which is incorporated herein by reference.

TECHNICAL FIELD

This disclosure is directed to the field of navigation of and maintaining position of medical devices, such as biopsy or ablation tools, relative to targets.

DESCRIPTION OF RELATED ART

There exist a number of platforms for navigation of catheters and tools within the lungs of a patient. Many of these platforms rely on a bronchoscope to perform some portion of the navigation and then allow tools or catheters to be inserted further into the lungs via the working channel.

However, both the catheter and the tools that can be inserted into the working channel can be incredibly long (e.g., in excess of a meter in length). This length creates some challenges for the user who needs to balance the bronchoscope while it is in the patient in one hand, and then manually feed the catheter into the bronchoscope. When a tool such as a biopsy tool is to be inserted into the catheter and through the bronchoscope, the procedure may in fact require a third hand, provided by a nurse or additional attendant to ensure that all of the components can be manipulated.

One of the more challenging aspects can be the insertion of a biopsy needle into a proximal end of the catheter that has been inserted into the bronchoscope. Because the bronchoscope is not fixed but is handheld the lumen in the catheter can be difficult to line up with the very long and flexible tool and insert into the catheter. Similarly, after performance of a procedure, these long tools require removal which can again crate challenges in handling. Accordingly, improvements are desired.

SUMMARY

One aspect of the disclosure is directed to a system for navigation of a lung including: an electromagnetic (EM) field generator. The system also includes a sensor located on a distal end of a catheter, the sensor configured to receive EM signals and transmit them to a locating module. The system also includes a computing device in communication with the locating module and configured to display a 3D model of the lungs and to depict the location of the catheter in the 3D model. The system also includes a cannister configured to retain the catheter in a coiled form within the cannister, the cannister having an entrance point centrally located on a top surface of the cannister and an exit point centrally located on a bottom surface of the cannister. The system also includes an arm configured to support the cannister. The system also includes a drive mechanism configured to advance the catheter from the cannister through the exit point and into the lungs of a patient, the drive mechanism including a pair of wheels configured to act on an exterior surface of the catheter. The system also includes an articulation motor mechanically coupled to a pair of pull-wires, the pull wires being retained within first lumens formed in the catheter, where actuation of the articulation motor results in articulation of a distal end of the catheter in at least one direction. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The system for navigation of a lung where the cannister further includes an entrance point, the catheter being located proximate the entrance point. The system for navigation of a lung further including two articulation motors, each articulation motor connected to a pair of pull-wires, the pull wires retained within four first lumens and configured to articulate the catheter in at least four orthogonal directions. The system for navigation of a lung further including a second cannister, the second cannister including a drive mechanism configured to drive a tool from the cannister via an exit point formed on a bottom of the second cannister. The system for navigation of a lung where the second cannister is configured to mate with the cannister such that when the tool is driven from the second cannister, it is driven into a central lumen of the catheter proximate the entrance point of the cannister. The system for navigation of a lung where the second cannister includes an entrance point. The system for navigation of a lung where the entrance point is formed on a side of the second cannister. The system for navigation of a lung where the tool is an imaging tool. The system for navigation of a lung where the tool is a therapeutic tool. The system for navigation of a lung where the tool is a biopsy tool. The system for navigation of a lung where the second cannister includes an entrance point in fluid communication with a lumen formed in the tool. The system for navigation of a lung where the tool is a biopsy device, and the entrance point on the second cannister is configured to receive a fluid or vacuum source. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

A further aspect of the disclosure is directed to a catheter system for use with a luminal navigation system including: a cannister configured to retain a catheter in a coiled form, the cannister having an entrance point and an exit point; a drive mechanism configured to advance the catheter from the cannister through the exit point and into a luminal network of a patient; and an articulation motor mechanically coupled to a pair of pull-wires, the pull wires being retained within first lumens formed in the catheter, where actuation of the articulation motor results in articulation of a distal end of the catheter in at least one direction.

Implementations of this aspect of the disclosure may include one or more of the following features. The catheter system further including a removable lid allowing access to an internal volume of the cannister for inserting or removing a catheter. The catheter system where the articulation motor is attached to the lid. The catheter system further including an entrance point formed on a side of the cannister and configured to receive a tool. The catheter system further including a support configured to mate with an arm to support the cannister proximate a head of a patient.

Yet another aspect of the disclosure is directed to a catheter system for use with a luminal navigation system including: a first cannister having an entrance point and an exit point; a disposable catheter configured for receipt and retention in the first cannister in a coiled form; a second cannister having an entrance point and an exit point; a flexible disposable tool configured for receipt and retention in the second cannister in a coiled form; a drive mechanism in the first cannister configured to advance the catheter from the first cannister through the exit point in the first cannister and into a luminal network of a patient; a drive mechanism in the second cannister configured to advance the tool through the exit point in the second cannister and into the entrance point of the first cannister and into a lumen in the disposable catheter; and an articulation motor mechanically coupled to a pair of pull-wires, the pull wires being retained within lumens formed in the disposable catheter, where actuation of the articulation motor results in articulation of a distal end of the catheter in at least one direction. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The catheter system where the flexible disposable tool is a tool selected from the group including of a biopsy tool, a therapeutic tool, or an imaging too. The catheter system where the entrance point of the second cannister is in fluid communication with a distal end of the flexible disposable tool enabling connection of a vacuum or fluid source to the flexible disposable tool. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

BRIEF DESCRIPTION OF THE DRAWINGS

Various aspects and embodiments of the disclosure are described hereinbelow with references to the drawings, wherein.

DETAILED DESCRIPTION

This disclosure is directed to a cannister based catheter and tool system which overcomes the challenges of the known system. By placing the catheter and tools in a cannister the longitudinal dimensions of the catheter and tool may be managed to reduce the burden of manipulating long and flexible catheters and tools. Further, by stacking cannisters a tool cannister may be placed on a catheter cannister. These cannisters may be used either with or without a bronchoscope to navigate the catheter to a desired location within the patient. Though described generally herein with respect to a cannister, the term should not be construed narrowly but rather should include any device capable of storing and advancing a catheter. As such, a cannister should be interpreted to include modules, cartridges, cassettes, and other such devices.

Figure 1:
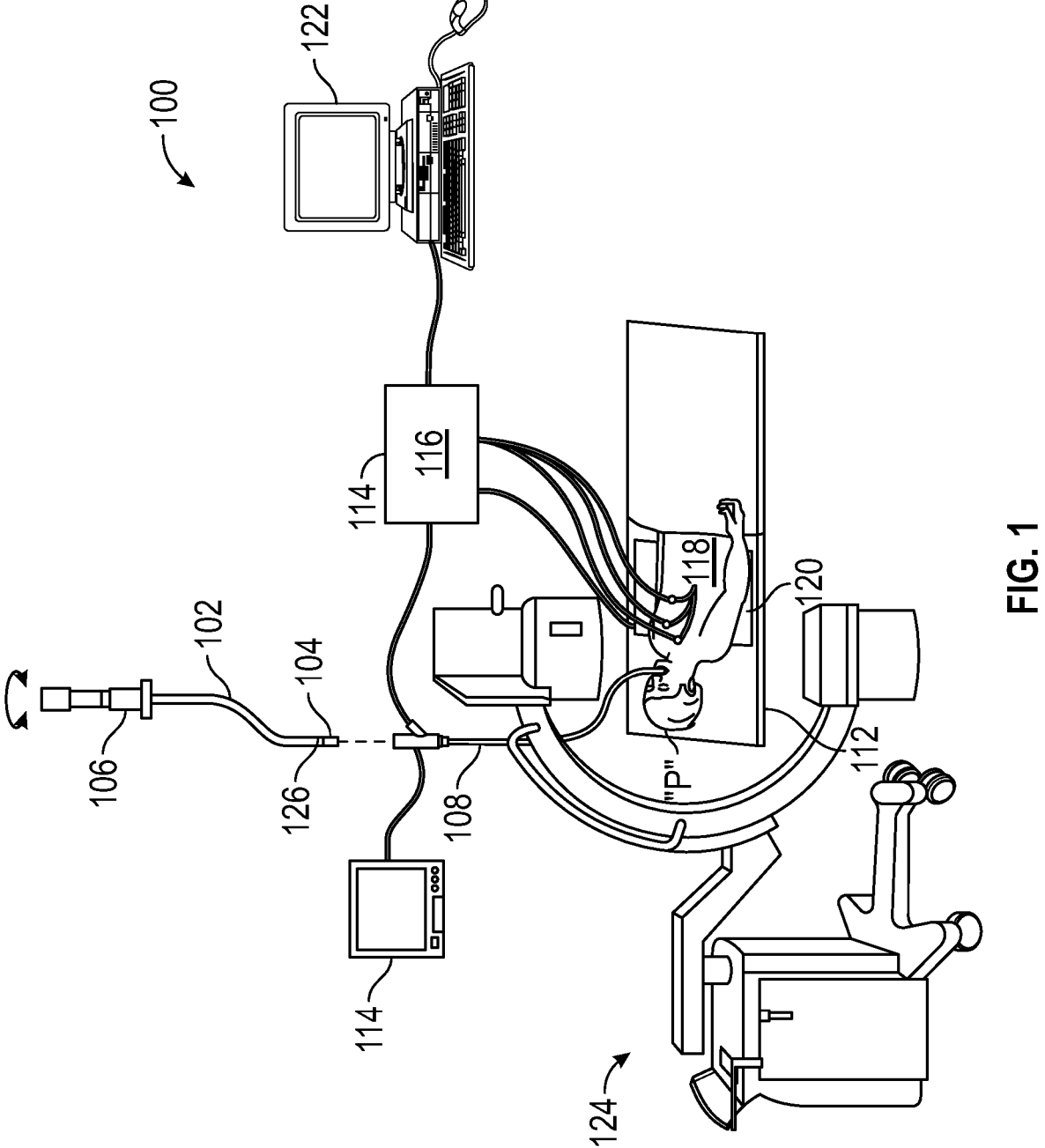
FIG. 1 is a schematic diagram of a system for navigating to soft tissue targets via luminal networks in accordance with the disclosure.

FIG. 1 is a perspective view of an exemplary system for facilitating navigation of a medical device, e.g., a catheter to a soft-tissue target via airways of the lungs. System 100 may be further configured to construct fluoroscopic based three-dimensional volumetric data of the target area from 2D fluoroscopic images to confirm navigation to a desired location. System 100 may be further configured to facilitate approach of a medical device to the target area by using Electromagnetic Navigation (EMN) and for determining the location of a medical device with respect to the target. One such EMN system is the ILLUMISITE system currently sold by Medtronic PLC, though other systems for intraluminal navigation are considered within the scope of the disclosure, as noted above.

One aspect of the system 100 is a software component for reviewing of computed tomography (CT) image scan data that has been acquired separately from system 100. The review of the CT image data allows a user to identify one or more targets, plan a pathway to an identified target (planning phase), navigate a catheter 102 to the target (navigation phase) using a user interface on computing device 122, and confirming placement of a sensor 104 relative to the target. The target may be tissue of interest identified by review of the CT image data during the planning phase. Following navigation, a medical device, such as a biopsy tool or other tool, may be inserted into catheter 102 to obtain a tissue sample from the tissue located at, or proximate to, the target.

As shown in FIG. 1, catheter 102 is part of a catheter guide assembly 106. In practice, catheter 102 is inserted into a bronchoscope 108 for access to a luminal network of the patient P. Specifically, catheter 102 of catheter guide assembly 106 may be inserted into a working channel of bronchoscope 108 for navigation through a patient's luminal network. A locatable guide (LG) 110 (a second catheter), including a sensor 104 is inserted into catheter 102 and locked into position such that sensor 104 extends a desired distance beyond the distal tip of catheter 102. The position and orientation of sensor 104 relative to a reference coordinate system, and thus the distal portion of catheter 102, within an electromagnetic field can be derived. Catheter guide assemblies 106 are currently marketed and sold by Medtronic PLC under the brand names SUPERDIMENSION® Procedure Kits, or EDGE™ Procedure Kits, and are contemplated as useable with the disclosure.

System 100 generally includes an operating table 112 configured to support a patient P, a bronchoscope 108 configured for insertion through patient P's mouth into patient P's airways; monitoring equipment 114 coupled to bronchoscope 108 (e.g., a video display, for displaying the video images received from the video imaging system of bronchoscope 108); a locating or tracking system 114 including a locating module 116, a plurality of reference sensors 18 and a transmitter mat 120 including a plurality of incorporated markers; and a computing device 122 including software and/or hardware used to facilitate identification of a target, pathway planning to the target, navigation of a medical device to the target, and/or confirmation and/or determination of placement of catheter 102, or a suitable device therethrough, relative to the target.

A fluoroscopic imaging device 124 capable of acquiring fluoroscopic or x-ray images or video of the patient P is also included in this particular aspect of system 100. The images, sequence of images, or video captured by fluoroscopic imaging device 124 may be stored within fluoroscopic imaging device 124 or transmitted to computing device 122 for storage, processing, and display. Additionally, fluoroscopic imaging device 124 may move relative to the patient P so that images may be acquired from different angles or perspectives relative to patient P to create a sequence of fluoroscopic images, such as a fluoroscopic video. The pose of fluoroscopic imaging device 124 relative to patient P and while capturing the images may be estimated via markers incorporated with the transmitter mat 120. The markers are positioned under patient P, between patient P and operating table 112 and between patient P and a radiation source or a sensing unit of fluoroscopic imaging device 124. The markers incorporated with the transmitter mat 120 may be two separate elements which may be coupled in a fixed manner or alternatively may be manufactured as a single unit. Fluoroscopic imaging device 124 may include a single imaging device or more than one imaging device. As an alternative a cone-beam CT imaging device may be employed without departing from the scope of the disclosure and can be used to confirm the location of a tool within the patient, update CT-based 3D modeling, or replaced pre-procedural 3D modeling with intra-procedural modeling of the patient's airways and the position of the catheter 102 within the patient.

Computing device 122 may be any suitable computing device including a processor and storage medium, wherein the processor is capable of executing instructions stored on the storage medium. Computing device 122 may further include a database configured to store patient data, CT data sets including CT images, fluoroscopic data sets including fluoroscopic images and video, fluoroscopic 3D reconstruction, navigation plans, and any other such data. Although not explicitly illustrated, computing device 122 may include inputs, or may otherwise be configured to receive, CT data sets, fluoroscopic images/video and other data described herein. Additionally, computing device 122 includes a display configured to display graphical user interfaces. Computing device 122 may be connected to one or more networks through which one or more databases may be accessed.

With respect to the planning phase, computing device 122 utilizes previously acquired CT image data for generating and viewing a three-dimensional model or rendering of patient P's airways, enables the identification of a target on the three-dimensional model (automatically, semi-automatically, or manually), and allows for determining a pathway through patient P's airways to tissue located at and around the target. More specifically, CT images acquired from previous CT scans are processed and assembled into a three-dimensional CT volume, which is then utilized to generate a three-dimensional model of patient P's airways. The three-dimensional model may be displayed on a display associated with computing device 122, or in any other suitable fashion. Using computing device 122, various views of the three-dimensional model or enhanced two-dimensional images generated from the three-dimensional model are presented. The enhanced two-dimensional images may possess some three-dimensional capabilities because they are generated from three-dimensional data. The three-dimensional model may be manipulated to facilitate identification of target on the three-dimensional model or two-dimensional images, and selection of a suitable pathway through patient P's airways to access tissue located at the target can be made. Once selected, the pathway plan, three-dimensional model, and images derived therefrom, can be saved, and exported to a navigation system for use during the navigation phase(s). The ILLUMISITE software suite currently sold by Medtronic PLC includes one such planning software.

With respect to the navigation phase, a six degrees-of-freedom electromagnetic locating or tracking system 114, or other suitable system for determining position and orientation of a distal portion of the catheter 102, is utilized for performing registration of the images and the pathway for navigation. Tracking system 114 includes the tracking module 116, a plurality of reference sensors 118, and the transmitter mat 120 (including the markers). Tracking system 114 is configured for use with a locatable guide 110 and particularly sensor 104. As described above, locatable guide 110 and sensor 104 are configured for insertion through catheter 102 into patient P's airways (either with or without bronchoscope 108) and are selectively lockable relative to one another via a locking mechanism.

Transmitter mat 120 is positioned beneath patient P. Transmitter mat 120 generates an electromagnetic field around at least a portion of the patient P within which the position of a plurality of reference sensors 118 and the sensor 104 can be determined with use of a tracking module 116. A second electromagnetic sensor 126 may also be incorporated into the end of the catheter 102. The second electromagnetic sensor 126 may be a five degree-of-freedom sensor or a six degree-of-freedom sensor. One or more of reference sensors 118 are attached to the chest of the patient P. Registration is generally performed to coordinate locations of the three-dimensional model and two-dimensional images from the planning phase, with the patient P's airways as observed through the bronchoscope 108 and allow for the navigation phase to be undertaken with knowledge of the location of the sensor 104.

Registration of the patient P's location on the transmitter mat 120 may be performed by moving sensor 104 through the airways of the patient P. More specifically, data pertaining to locations of sensor 104, while locatable guide 110 is moving through the airways, is recorded using transmitter mat 120, reference sensors 118, and tracking system 114. A shape resulting from this location data is compared to an interior geometry of passages of the three-dimensional model generated in the planning phase, and a location correlation between the shape and the three-dimensional model based on the comparison is determined, e.g., utilizing the software on computing device 122. In addition, the software identifies non-tissue space (e.g., air filled cavities) in the three-dimensional model. The software aligns, or registers, an image representing a location of sensor 104 with the three-dimensional model and/or two-dimensional images generated from the three-dimension model, which are based on the recorded location data and an assumption that locatable guide 110 remains located in non-tissue space in patient P's airways. Alternatively, a manual registration technique may be employed by navigating the bronchoscope 108 with the sensor 104 to pre-specified locations in the lungs of the patient P, and manually correlating the images from the bronchoscope to the model data of the three-dimensional model.

Though described herein with respect to EMN systems using EM sensors, the instant disclosure is not so limited and may be used in conjunction with flexible sensor, shape sensors such as Fiber-Bragg gratings, ultrasonic sensors, or without sensors. Additionally, the methods described herein may be used in conjunction with robotic systems such that robotic actuators drive the catheter 102 or bronchoscope 108 proximate the target.

At any point during the navigation process a tool such as a biopsy tool or a therapy tool including for example microwave ablation tools may be inserted into the catheter 102 to place the tool proximate the desired target.

Figure 2:
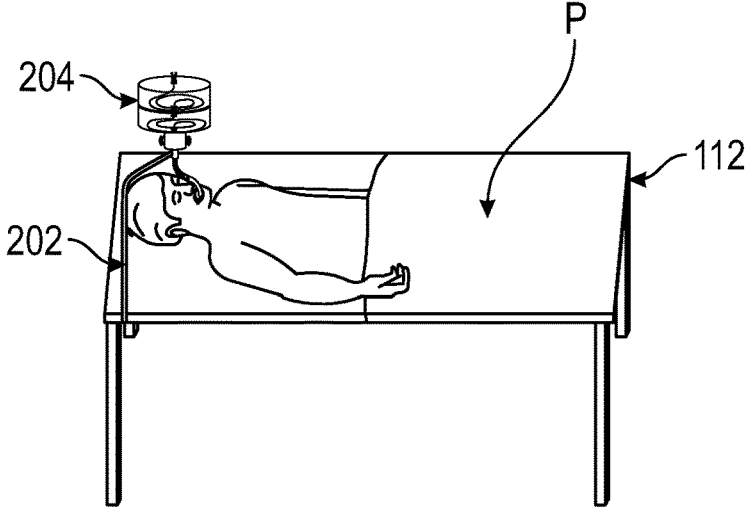
FIG. 2 is a schematic diagram of a cannister system in accordance with the disclosure.

FIG. 2 depicts an aspect of the disclosure. In FIG. 2, the patient P is located on an operating table 112. All of the features of FIG. 1 are also employed in the system of FIG. 2, and are not repeated here, except for the bronchoscope 108. An arm 202, or other stabilizing feature such as a U-shape can be placed over and proximate a head of the patient and is secured to the operating table 112. A cannister 204 is secured to the arm 202 and configured to allow a catheter 102 that is located therein to extend out of the cannister 204 and into a luminal network, such as the airways of the patient. Tracking of the catheter 102 (e.g. using the EM field generated by the transmitter matt 120, and a sensor 104, 126 associated with the catheter) and updating of the location of the catheter 102 in a 3D model is the same as that described in the system of FIG. 1. Though shown here as connected to the table 112, the arm 202 is not so limited and may be floor mounted, mounted on a caster system, or other configurations allowing the arm 202 and cannister 204 supported thereon to be brough into proximity of the patient.

Figure 3:
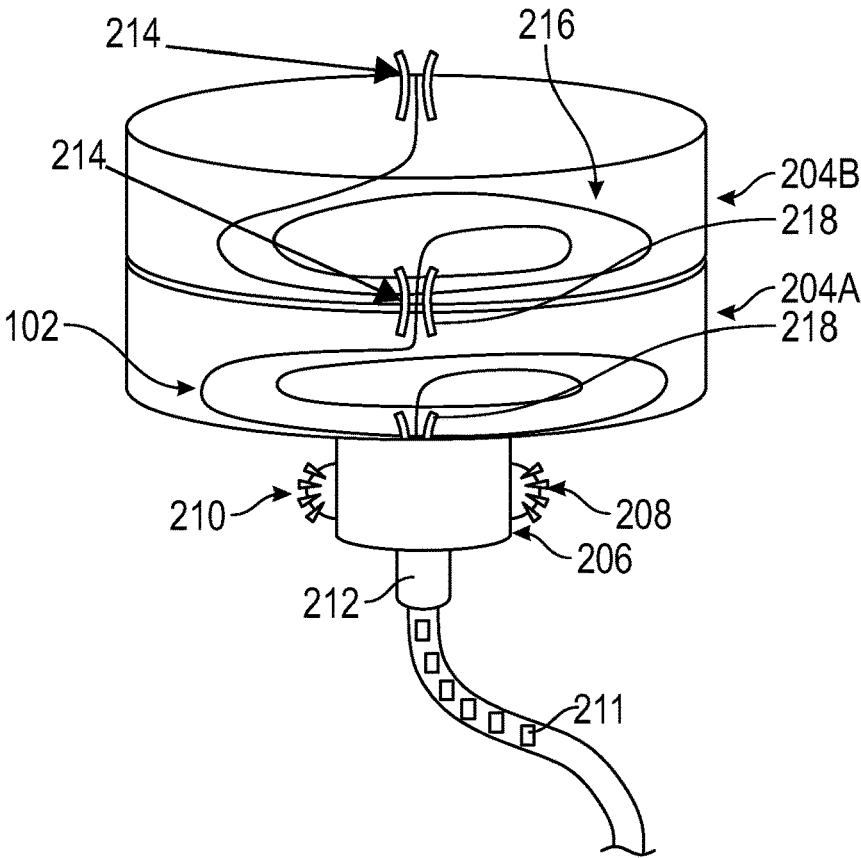
FIG. 3 is a plan view of a pair of cannisters in accordance with the disclosure.

FIG. 3 depicts a tool cannister 204B placed on top of a catheter cannister 204A. In the configuration of FIG. 3 a drive device 206 is formed outside of the cannister 204A. The drive mechanism 206 may be for example a pair of motor driven wheels 208. In one embodiment the wheels 208 are formed with protrusions 210 which engage corrugations or embossing 211 formed on the catheter 102. The motor driven wheels 208 engage the catheter 102 to advance the catheter 102 into the luminal network of the patient (e.g., the lungs). As will be described in greater detail below, though the drive mechanism 206 is shown exterior to the catheter cannister 204A, the drive mechanism 206 may be formed internal to the catheter cannister 204A and the tool cannister 204B. A support 212 is configured to be attached to the arm 202 and held in place relative to the patient P. The motor driven wheels 208 may also be smooth or without protrusions and instead rely on their proximity to each other to compress the exterior of the catheter to ensure engagement therewith. Additionally or alternatively the materials of the motor driven wheels 208 may be selected based on their coefficient of friction such that the driven wheels 208 engage and drive the catheter 102 to ensure sufficient grip. Either the driven wheels 208 or the catheter 102 may also be roughened to increase their respective coefficient of friction.

In the embodiment of FIG. 3, an entrance point 214 for the catheter 102 in the catheter canister 204A is on the centerline of the cannister. The entrance point 214 fluidly connects a lumen in the catheter 102 and allows for the insertion of a tool 216 from the tool cannister 204B to be inserted into the catheter 102 of the catheter cannister 204A. An exit point 218 from the catheter cannister 204A is on the centerline of the cannister. This exit point 218, allows the catheter 102 to be driven out of or pulled from the catheter cannister 204A by the drive device 206. The tool 216 is similarly in a coiled form in the tool cannister 204B. This construction significantly reduces the awkwardness of long catheters and tools by providing the catheter 102 and tool 216 in a coiled form in the catheter cannister 204A and the tool cannister 204B. The tool 216, may be secured to the cannister 204B at the entrance point 214 or another location in the tool cannister 204B and prevented from passing entirely through the entrance point 214 of the catheter cannister 204A. The exit point 218 of the tool cannister 204B aligns with the entrance point 214 of the catheter cannister 204A and allows for the tool 216 to be extended out of the tool cannister 204B into the catheter 102 in the catheter cannister 204A, and ultimately through the catheter 102 to a target location within the patient. A proximal end of the tool 216 may be secured to the entrance point 214 of the tool cannister 204B and allow for, among other things, fluid communication with the distal end of the tool 216. For example, where aspiration or suction is required, a syringe may be connected to the entrance point to enable the application and withdrawal of fluid for securing a biopsy sample.

Figure 4:
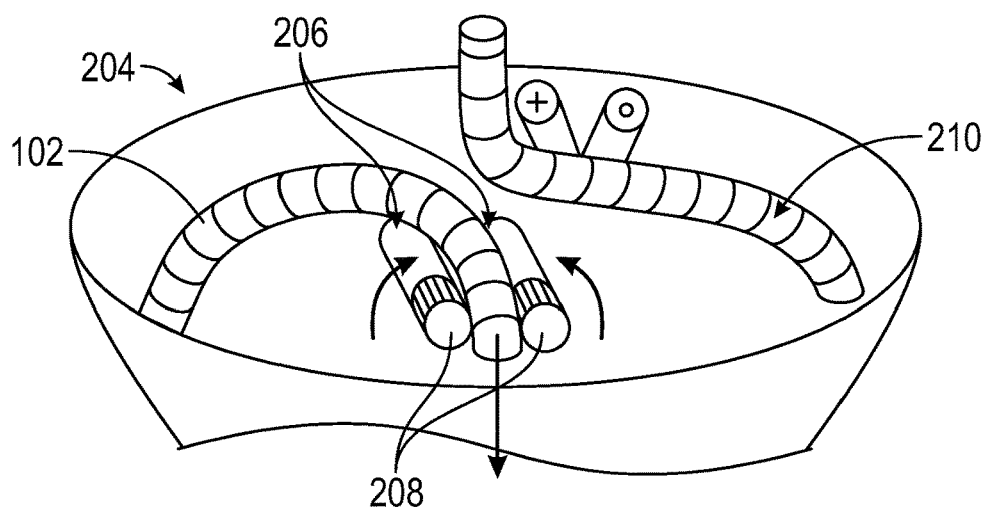
FIG. 4 is a perspective view of a cannister in accordance with the disclosure.

FIG. 4 depicts a perspective view of the internals of a cannister 204 either the tool cannister 204B or the catheter cannister 204A. As noted above, the drive mechanism 206 may be placed within the cannister 204. The drive mechanism 206 may be in the form of two drive motors that propel drive wheels 208 to advance and retract the catheter 102 or the tool 216 from the cannister. As noted above, corrugations 210 or other features embossed or formed into the catheter 102 or the tool 216 can assist in their being gripped by the drive wheels 208. In some instances, the catheter 102 or tool 216 may not be embossed or corrugated and may just rely on the gripping force of the drive wheels 208 acting on the catheter 102 or tool 216.

The materials for the catheter 102 and the tool 216 may be selected so that when driven by the drive wheels 208, particularly in retraction they coil appropriately within the catheter cannister 204A and the tool cannister 204B. Thus, to enable navigation within the patient, the catheter cannister 204A can be secured to the arm 202 via support 212. The drive mechanism 206 can receive signals via an actuator (not shown) which may be on the cannister and manually operated by the user or electrically connected to a computer-controlled system to provide the drive signals to the drive mechanism 206.

In one embodiment, only the catheter cannister 204A is employed and traditional tools 216 (e.g., a biopsy tool) is inserted into the entrance point 214 and manually advanced into the catheter 102 that has been navigated to a desired location within the patient. By securing the catheter cannister 204 to the arm 202 and providing a consistently located and non-moving entrance point 214 at a convenient location to the user, the acquisition of a biopsy or the insertion of a therapy tool such as a microwave ablation antenna can be easily inserted and passed through the catheter 102 to reach the desired location within patient.

Alternatively, a second cannister such as the tool cannister 204B can be employed. The tool cannister 204B may include any form of tool 216. These tools 216 may be biopsy tools such including brushes, coring tools, fine needle aspirators, imaging tools including optical, fiber optic, ultrasound, and others, as well as therapy tools including microwave ablation catheter, vessel sealers, cryoablation tools, radio frequency ablation tools, and others. For example, during an initial navigation of the catheter 102 the tool cannister 204B may include an imaging tool 216. The imaging tool 216 may be advanced in combination with the catheter 102. That is the imaging tool 216 may be driven by the drive mechanism 206 in the tool cannister 204B simultaneously with the drive mechanism 206 in the catheter cannister 204A to advance the catheter 102. Upon completion of the use of the imaging tool 216, for example, after navigating to a target within the patient, the imaging tool 216 may be retracted using the drive mechanism 206 in the tool cannister 204B. After complete retraction of the tool 216, the tool cannister 204B may be removed from its interface with the catheter cannister 204A and another tool cannister 204B placed in its place on the catheter cannister 204A, this second cannister may be for example a tool cannister 204B in which the tool is a biopsy tool 216. With the catheter 102 proximate the target, the biopsy tool 216 may be driven from the tool cannister 204B through the exit point 218 and into the entrance point 214 of the catheter cannister 204A through the catheter 102 to arrive at the end of the catheter 102 proximate the target. As will be appreciated the drive mechanism 206 in the catheter cannister 204A prevents movement of the catheter 102 in the longitudinal direction while for example the drive mechanism 206 in the tool cannister 204B drives the tool 216 through the catheter.

Figure 5A:
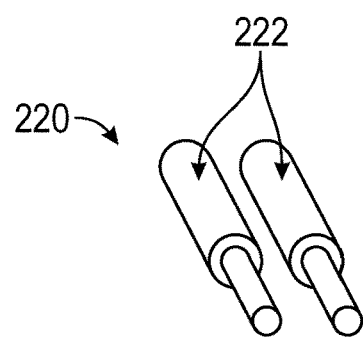
FIGS. 5A-5C depict an articulation system employed by a cannister in accordance with the disclosure.
Figure 5B:
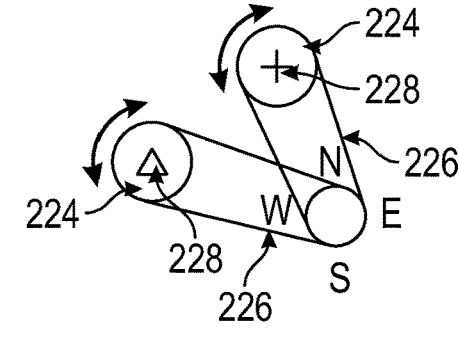
Figure 5C:
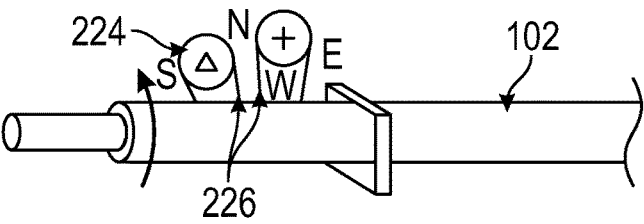

Another aspect of the disclosure is an articulation mechanism depicted in FIGS. 5A-5C. A lid 220 of a cannister 204 is shown in FIG. 5A. Extending from the lid 220 are articulation motors 222. The articulation motors 222 in the lid are each configured to mate with a pulley 224. Connected to each pulley 224 are a pair of pull wires 226. Each pair of pull wires 226 is routed through lumens formed in the catheter 102 which terminate proximate a distal end of the catheter 102. The pull wires 226 enable articulation of the catheter 102. The pull wires 226 may be formed of a single wire, both ends of which are terminated proximate the distal end of the catheter 102. The pull wires 226 exit the lumens (not shown) formed in the catheter 102 and loop over the pulley 224. Rotation of the pulley 224 causes one of the pull wires 226 in the pair to be pulled and a second to be pushed. This push and pull enables articulation of the catheter in a single direction. Rotation of the pulley 224 in a second direction allows the catheter 102 to return to the un-articulated position and if rotation is continued to articulate in a second direction. By formation of the lumens in which the pull-wires 226 are routed approximately 180 degrees from one another, these two directions are substantially opposite directions of articulation (e.g., North and South). A second pair of pull-wires 226 may be included to enable articulation in two additional directions (e.g., East and West). Those of skill in the art will recognize that by actuating both sets of pull wires enables articulation in nearly any direction. The pulleys 224 may each include a separate key 228 configured to mate with a corresponding feature on the articulation motors 222. The use of the keys 228 ensure that the proper pull wires 226 are mated with the proper articulation motors 222, particularly where the catheter 102 is disposable and the cannister 204 is reusable, as described below.

Though the term pull-wire is used herein to describe the pull-wire 226, the term is not so limited and should be interpreted to include pull members, tethers, extrusions, plastics, and other thread or wire like elements that can be used to connect the articulation motors to the distal portions of the catheters 102.

Figure 6:
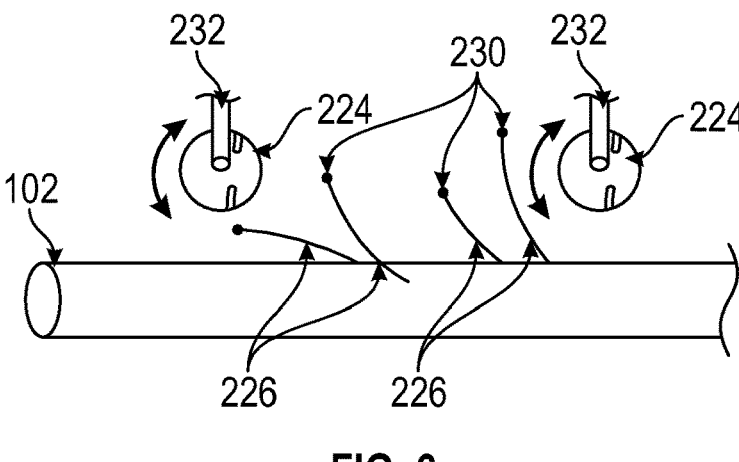
FIG. 6 a schematic view of a second articulation system employed by a cannister in accordance with the disclosure.

As an alternative to the pulleys 224 being mated with the pull wires 226, the pulleys 224 may be affixed to the articulation motors 220 as shown in FIG. 6. Ends of the pull wires 226 may include crimps or welded balls 230 on their ends. The crimps or welded balls 230 may be received in holes 232 on the pulleys 224. In this manner the pulleys 224 remain part of the cannister 204. Articulation of the tool 216 may also be enabled via articulation motors 222 in the tool cannister 204B and pull wires 226 in the tools 216, however, they are not required as articulation of the tool 216 can be enabled by the articulation of the catheter 102 through which it passes.

In accordance with one aspect of the disclosure, the articulation motors 222 can be used to control the orientation of the catheter 102 such that the catheter 102 is pointed at a target. Once so placed, the catheter 102 may be locked in place. The drive mechanism 206 of the tool cannister 204B may then be used to drive to the tool 216 such that it is proximate the distal end of the catheter 102 and possibly extend slightly therefrom. Once so placed the location of the tool 216 proximate the target can be confirmed with one or more imaging modalities (e.g., a fluoroscopy or a Cone Beam Computed Tomography). Upon confirmation, the drive mechanism 206 may be driven at a very high speed to effectuate insertion into the target. The use of speed for navigation and a second speed for target insertion enables the tool 216 to make use of the resilience of the tissue to enable clean insertion. Clean insertion helps ensure that it is in fact the tissue of the target that is sampled in a biopsy, cleaner edges are revealed to allow for better examination, and other benefits known to those of ordinary skill in the art.

The catheter 102 and tool 216 may be a completely separate and disposable component separate from the catheter cannister 204A of the tool cannister 204B. The distal end of catheter 102 or tool 216 may be inserted into the drive mechanism 206 and optionally advanced through the exit point 218 of the cannister 204A or 204B. The catheter 102 or tool 215 may be manually coiled into the catheter cannister 204A and tool cannister 204B, respectively. The interior of the cannisters 204 may include embossing, molding, or other features to assist in formation of a consistent coil of the catheter 102 or tool 216 along the interior of the cannister. The proximal end of the catheter 102 is secured to the lid 220 proximate the entrance point 214, to allow access to the lumen of the catheter 102 and when a tool 216 and a tool cannister 204B is mated with the catheter cannister 204A. The proximal end of the tool 216 may be secured proximate the entrance point 214 to allow fluid connection to the tool 216. The cannisters 204A and 204B may be sterilized after use and removal of the catheter 102 or tool 216 through known techniques including UV, ultrasonic, ozone, radiation, and others.

Figure 7:
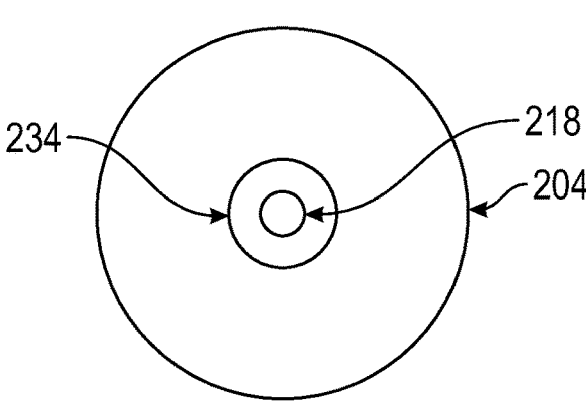
FIG. 7 is a top view of a cannister in accordance with the disclosure.

To further assist in the catheter 102 or tool 216 to conveniently coil in the cannister 204A or 204B, a bearing 234 may be employed. The bearing 234 may be mounted in the bottom of the cannister 204 proximate the exit point 218, as shown in FIG. 7. The drive mechanism 206 may be mounted on the bearing 234 such that the drive mechanism 206 rotates relative to the cannister 204. In this fashion an orientation of the catheter 102 to the drive mechanism 206 may be maintained to ensure that when the catheter 102 is driven out of the cannister 204 or retracted back into the cannister 204 the catheter 102 is coiled appropriately and no inadvertent overlaps or entanglements result. This is particularly important for the catheter 102 as in practice, the catheter 102 may be navigated to a variety of locations within the patient to collect samples and to perform therapies. Thus, accurate and consistent placement of the catheter 102 within the cannister 204A is necessary. However, it is also true for the tools 216, particularly therapy tools 216 which may be used in a number of locations within the patient in a single therapy session.

As noted above, the drive mechanisms 206 of the catheter cannister 204A and of the tool cannister 204B may be manually operated using switches or toggles on the cannisters 204A and 204B. In addition, there may be interlocks between the two drive mechanisms 206 where for example the catheter 102 is prevented from retracting more than a specified distance when the tool 216 is extended through the catheter 102. Similarly, the actuation of the drive mechanisms 206 may be configured for simultaneous actuation in certain instances, such as during navigation of an imaging probe within the patient. In such situations it is desirable for both catheter 102 and tool 216 to advance together.

Still further, the advancement and retraction of the catheter 102 and tools 216 may be controlled via an application stored in memory on the computing device and executed by a processor therein. The application can provide for virtual controls of the drive mechanisms 206 and the actuation motors 222 to allow for computerized control of the catheter 102 and the tools 216. Still further, the computing device 122 may include one or more applications which in combination with the planning and navigation software described above, can be utilized to automatically drive the catheter to a desired location within the patient, and then execute a biopsy or therapy using the tool 216.

Figure 8:
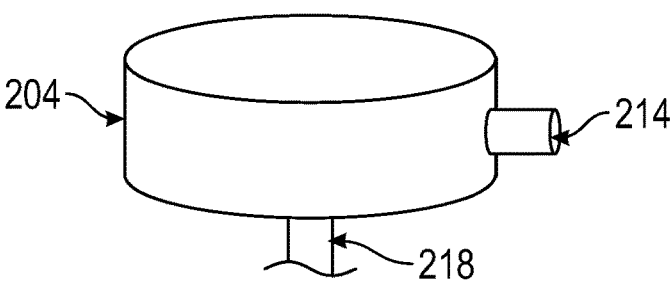
FIG. 8 is a side view of a cannister in accordance with the disclosure.

Though described herein as requiring the entrance point 214 to be on a top of the cannister 204, the disclosure is not so limited. For example, as shown in FIG. 8 the catheter cannister 204A, particularly in embodiments where the tools 216 are manually inserted into the catheter 102, may have an entrance point 214 on a side of the cannister.

Still further, though described herein as employing a pair of pull-wires 206, in a further embodiment, the cannister 204 or 204A may itself rotate. As a result, a pair of pull-wires 206 is not required, rather sufficient articulation can be achieved with a single pull-wire 206. This is true whether the rotation is achieved by the user's hand, by a gear mechanism, or a motor driven embodiment.

Though generally described herein with respect to navigation within the lungs of a patient, the disclosure is not so limited. The systems and methods described herein may be utilized to access any luminal network of the patient including the biliary, gastro-intestinal, venous, arterial, lymphatic, urinary, and other luminal networks of the body without departing from the scope of the disclosure.

While detailed embodiments are disclosed herein, the disclosed embodiments are merely examples of the disclosure, which may be embodied in various forms and aspects. For example, embodiments of an electromagnetic navigation system, which incorporates the target overlay systems and methods, are disclosed herein; however, the target overlay systems and methods may be applied to other navigation or tracking systems or methods known to those skilled in the art. Therefore, specific structural and functional details disclosed herein are not to be interpreted as limiting, but merely as a basis for the claims and as a representative basis for teaching one skilled in the art to variously employ the disclosure in virtually any appropriately detailed structure.

We claim:
1. A system for navigation of a lung comprising:
an electromagnetic (EM) field generator;

a sensor located on a distal end of a catheter, the sensor configured to receive EM signals and transmit them to a locating module;

a computing device in communication with the locating module and configured to display a 3D model of the lungs and to depict the location of the catheter in the 3D model;

a cannister configured to retain the catheter in a coiled form within the cannister, the cannister having an entrance point centrally located on a top surface of the cannister and an exit point centrally located on a bottom surface of the cannister;

an arm configured to support the cannister;

a drive mechanism configured to advance the catheter from the cannister through the exit point and into the lungs of a patient, the drive mechanism including a pair of driven wheels, the pair of driven wheels contacting opposite sides of the catheter and configured to act on an exterior surface of the catheter; and a first articulation motor mechanically coupled to a first pair of pull-wires, the first pair of pull wires being retained within a first pair of lumens formed in the catheter, wherein actuation of the articulation motor results in articulation of a distal end of the catheter in at least one direction.

2. The system for navigation of a lung of claim 1, wherein the catheter further includes an entrance point, the entrance point of the catheter being located proximate the entrance point of the cannister.

3. The system for navigation of a lung of claim 1, further comprising a second articulation motor connected to a second pair of pull-wires, the second pair of pull wires being retained within a second pair of lumens of the catheter, wherein the first and second articulation motors are configured to articulate the catheter in at least four orthogonal directions.

4. The system for navigation of a lung of claim 1, further comprising a second cannister, the second cannister including a second drive mechanism configured to drive a tool from the second cannister via a second exit point formed on a bottom of the second cannister.

5. The system for navigation of a lung of claim 4, wherein the second cannister is configured to mate with the cannister such that when the tool is driven from the second cannister, it is driven through the entrance point of the catheter and into a central lumen of the catheter proximate the entrance point of the cannister.

6. The system for navigation of a lung of claim 5, wherein the second cannister includes a second entrance point.

7. The system for navigation of a lung of claim 6, wherein the second entrance point is formed on a side of the second cannister.

8. The system for navigation of a lung of claim 5, wherein the tool is an imaging tool.

9. The system for navigation of a lung of claim 5, wherein the tool is a therapeutic tool.

10. The system for navigation of a lung of claim 5, wherein the tool is a biopsy tool.

11. The system for navigation of a lung of claim 10, wherein the second cannister includes an entrance point in fluid communication with a lumen formed in the tool.

12. The system for navigation of a lung of claim 11, wherein the tool is a biopsy device, and the entrance point on the second cannister is configured to receive a fluid or vacuum source.

13. A catheter system for use with a luminal navigation system comprising:

a cannister configured to retain a catheter in a coiled form, the cannister having an entrance point and an exit point;

a drive mechanism including a pair of drive wheels, the pair of driven wheels contacting opposite sides of the catheter and configured to advance the catheter from the cannister through the exit point and into a luminal network of a patient; and an articulation motor mechanically coupled to a pair of pull-wires, the pull wires being retained within lumens formed in the catheter, wherein actuation of the articulation motor results in articulation of a distal end of the catheter in at least one direction.

14. The catheter system of claim 13, further comprising a removable lid allowing access to an internal volume of the cannister for inserting or removing a catheter.

15. The catheter system of claim 14, wherein the articulation motor is attached to the lid.

16. The catheter system of claim 13, further comprising an entrance point formed on a side of the cannister and configured to receive a tool.

17. The catheter system of claim 13 further comprising a support configured to mate with an arm to support the cannister proximate a head of a patient.

18. A catheter system for use with a luminal navigation system comprising:

a first cannister having an entrance point and an exit point;

a disposable catheter configured for receipt and retention in the first cannister in a coiled form;

a second cannister having an entrance point and an exit point;

a flexible disposable tool configured for receipt and retention in the second cannister in a coiled form;

a drive mechanism in the first cannister including a pair of driven wheels, the pair of driven wheels contacting opposite sides of the catheter and configured to advance the catheter from the first cannister through the exit point in the first cannister and into a luminal network of a patient;

a drive mechanism in the second cannister configured to advance the tool through the exit point in the second cannister and into the entrance point of the first cannister and into a lumen in the disposable catheter; and an articulation motor mechanically coupled to a pair of pull-wires, the pull wires being retained within lumens formed in the disposable catheter, wherein actuation of the articulation motor results in articulation of a distal end of the catheter in at least one direction.

19. The catheter system of claim 18, wherein the flexible disposable tool is a tool selected from the group consisting of a biopsy tool, a therapeutic tool, or an imaging tool.

20. The catheter system of claim 18 wherein the entrance point of the second cannister is in fluid communication with a distal end of the flexible disposable tool enabling connection of a vacuum or fluid source to the flexible disposable tool.

* * * * *